(12) United States Patent
Hoeg et al.

(10) Patent No.: US 9,763,563 B2
(45) Date of Patent: Sep. 19, 2017

(54) ENDOSCOPIC CAMERA SINGLE-BUTTON MODE ACTIVATION (75) Inventors: Hans David Hoeg, Vancouver, WA (US); William S. Schnorr, Manhattan Beach, CA (US)

(73) Assignee: Karl Storz Imaging, Inc., Goleta, CA (US)

(*) Notice: Subject to any disclaimer, the term of this patent is extended or adjusted under 35 U.S.C. 154(b) by 0 days.

(21) Appl. No.: 13/546,623

(22) Filed: Jul. 11, 2012

(65) Prior Publication Data

US 2014/0018622 A1 Jan. 16, 2014

(51) Int. Cl.
*A61B 1/06* (2006.01)
*A61B 1/04* (2006.01)
*A61B 1/00* (2006.01)

(52) U.S. Cl.
CPC .............. *A61B 1/00181* (2013.01)

(58) Field of Classification Search
CPC ............ A61B 1/00174; A61B 1/00177; A61B 1/00179; A61B 1/00181; A61B 1/00183; A61B 1/00006; A61B 1/00066; A61B 1/00172; A61B 1/00039; A61B 5/7475
USPC .................................................. 600/173, 174
See application file for complete search history.

(56) References Cited

U.S. PATENT DOCUMENTS

| | | | |
|---|---|---|---|
| 4,692,608 A | 9/1987 | Cooper et al. | |
| 4,858,002 A | 8/1989 | Zobel | |
| 5,185,667 A | 2/1993 | Zimmermann | |
| 5,313,306 A | 5/1994 | Kuban et al. | |
| 5,359,363 A | 10/1994 | Kuban et al. | |
| 5,384,588 A | 1/1995 | Martin et al. | |
| 5,800,341 A | 9/1998 | McKenna et al. | |
| 5,818,527 A | 10/1998 | Yamaguchi et al. | |
| 5,954,634 A | 9/1999 | Igarashi | |
| 6,002,430 A | 12/1999 | McCall et al. | |
| 6,294,775 B1 | 9/2001 | Seibel et al. | |
| 6,364,830 B1 | 4/2002 | Durell | |
| 6,449,103 B1 | 9/2002 | Charles | |
| 6,638,216 B1* | 10/2003 | Durell | 600/173 |
| 7,344,494 B2 | 3/2008 | Hoeg et al. | |
| 7,382,399 B1 | 6/2008 | McCall et al. | |
| 7,427,263 B2 | 9/2008 | Hoeg et al. | |

(Continued)

FOREIGN PATENT DOCUMENTS

EP 0286733 A2 10/1988
JP 2066511 A 3/1990

(Continued)

OTHER PUBLICATIONS

European Search Report Application No. EP 13 17 3730 Completed: Oct. 8, 2013; Mailing Date: Oct. 17, 2013 4 pages.

*Primary Examiner* — Alexandra Newton
(74) *Attorney, Agent, or Firm* — Whitmyer IP Group LLC (57) ABSTRACT

A variable direction of view endoscope system including an endoscope having an image receiver with a variable direction of view adjustable over a viewing range bound by a first limit and a second limit and a single button for adjusting the variable direction of view of the image receiver, wherein actuation of the single button advances the variable direction of view sequentially through the viewing range. When the image receiver is at the second limit of the viewing range, actuation of the single button adjusts the image receiver back to the first limit of the viewing range.

16 Claims, 5 Drawing Sheets

(56) References Cited

U.S. PATENT DOCUMENTS

| | | |
|---|---|---|
| 8,167,795 B2 | 5/2012 | Hoeg et al. |
| 2001/0018553 A1* | 8/2001 | Krattiger et al. ............ 600/173 |
| 2001/0019361 A1 | 9/2001 | Savoye |
| 2003/0176778 A1* | 9/2003 | Messing ............... A61B 18/00 600/374 |
| 2004/0127769 A1 | 7/2004 | Hale et al. |
| 2005/0058360 A1 | 3/2005 | Berkey et al. |
| 2005/0113643 A1 | 5/2005 | Hale et al. |
| 2005/0119527 A1* | 6/2005 | Banik et al. ................. 600/117 |
| 2005/0197535 A1 | 9/2005 | Hoeg et al. |
| 2009/0143646 A1* | 6/2009 | Vail, III ....................... 600/135 |
| 2010/0010301 A1 | 1/2010 | Hale et al. |
| 2012/0116158 A1 | 5/2012 | Hale et al. |
| 2012/0245569 A1* | 9/2012 | Papac ................. A61F 9/00763 606/1 |
| 2014/0276207 A1* | 9/2014 | Ouyang et al. ............... 600/567 |

FOREIGN PATENT DOCUMENTS

| | | |
|---|---|---|
| JP | 10290777 A | 11/1998 |
| JP | 2000325307 A | 11/2000 |
| JP | 2007509710 A | 4/2007 |

* cited by examiner

ENDOSCOPIC CAMERA SINGLE-BUTTON MODE ACTIVATION

FIELD OF THE INVENTION

The present invention relates to endoscopes, and specifically to the user interface for controlling the viewing direction of modern variable direction of view endoscopes comprising electronics.

BACKGROUND OF THE INVENTION

Variable direction of view endoscopes allow a user to change the endoscopic viewing direction without having to change the position of the endoscope itself. Such endoscopes are useful when the user wants to see structures which are beside or behind the tip of the endoscope but can not easily move the endoscope shaft because of anatomical constraints or constraints imposed by other surgical instruments in the operative field.

Variable direction of view endoscopy is desirable because it affords surgeons greater flexibility in their procedural approach. Increased viewing mobility improves the quality of diagnoses, as in cystoscopy for example, where a typical diagnostic screening involves inspecting the interior surface of the bladder for lesions or tumors. The ability to look laterally and retrograde is important when doing this type of diagnosis because it makes it possible to visually cover the entire bladder surface, including the entrance region near the bladder neck. In ear-nose-throat and neurosurgical procedures, variable viewing is desired because the procedures are delicate, and the entrance ports are small. It is therefore not possible to manipulate the endoscope significantly without injuring the patient. The ability to look sideways and backwards is important however during and after tumor resection when it is necessary to keep track of tumor fragments, which if not caught can nucleate new tumors. Laparoscopy, another surgical discipline, imposes fewer maneuvering constraints but still benefits markedly from variable direction viewing because it allows surgeons to get better observation angles during a procedure and increases diagnostic capabilities. Also, because of the greater viewing versatility, variable direction of view endoscopes can minimize conflicts with other tools and can simplify surgical planning by their ability to achieve standard viewing angles from nonstandard positions, allowing the surgeon to keep the endoscope "off to the side" but still get the desired view.

With commercially available variable direction of view endoscopes, the user typically changes the line of sight by using knobs or levers which mechanically actuate optomechanics at the tip of the scope. For example, commonly owned U.S. Pat. No. 7,427,263 includes examples of variable direction of view endoscopes actuated by knobs and levers. Rotating a knob or moving a lever back and forth between two limits moves the endoscopic line of sight back and forth within a viewing range. The problems with knobs and levers are that they are complex, costly and insufficiently robust. As also shown in U.S. Pat. No. 7,427,263, electromechanical and electronic variable direction of view endoscopes may also be controlled with joysticks or buttons. A minimum of two buttons are typically used to achieve back and forth (and/or side to side) motion of the line of sight. There are often additional buttons for features such as quick return to a specified angle or to control other features, such as image capture, image-leveling, and illumination intensity.

The problem with multiple buttons is that users frequently press the wrong button because they are looking at a screen displaying the endoscopic image rather than at the buttons on the endoscope. Surgeons therefore express frustration with variable direction of view prototypes which have too many buttons. This frustration is the same as the long standing frustration surgeons have had with endoscopic camera heads which often have multiple buttons. Inevitably an incorrect button press occurs (or an incorrect joystick move) which invokes a function or move which then has to be undone.

Thus, there exists a need in the art for an improved means to control variable direction of view endoscopes.

SUMMARY OF THE INVENTION

Accordingly, it is an object of the invention to provide an improved endoscope that solves the above mentioned problems. It is a further object of the invention to provide an endoscope with a single button for adjusting the line of sight of a variable direction of view endoscope. Instead of having two buttons to move back and forth through the viewing range, a single button provides a single direction traverse of the viewing range with a wrap-around to the beginning once the edge of travel has been reached.

These and other objects of the invention are achieved by providing a variable direction of view endoscope system, including an endoscope with a view control device that adjusts a variable view angle of the endoscope between a plurality of view angle positions relative to the endoscope, and a single button for supplying a command that causes the view control device to adjust the view angle from a first one of the view angle positions to a second of the view angle positions. Each subsequent actuation of the single button causes the view controlling device to adjust the view angle to a next one of the view angle positions. In some embodiments, when the variable view angle is positioned in a last one of the plurality of view angle positions, actuation of the single button causes the view control device to adjust the view angle position back to the first one of the view angle positions.

In some embodiments, the single button is also used for capturing an image via the endoscope. A short button press, pressed for less than a predetermined amount of time, adjusts the view angle while a long button press, pressed for at least the predetermined amount of time, captures an image.

Other objects of the invention are achieved by providing a variable direction of view endoscope system, including an endoscope having an image receiver with a variable direction of view adjustable over a viewing range bound by a first limit and a second limit, and a single button for adjusting the variable direction of view of the image receiver, wherein actuation of the single button advances the variable direction of view sequentially through the viewing range. In some embodiments, when the image receiver is at the second limit of the viewing range, actuation of the single button adjusts the image receiver back to the first limit of the viewing range. The image receiver may include one of a CCD image sensor and a CMOS image sensor.

In some embodiments, the single button is also used for capturing images via the endoscope. A short button press, pressed for less than a predetermined amount of time, adjusts the view angle while a long button press, pressed for at least the predetermined amount of time, captures an image.

In some embodiments, the single button is on a proximal handle section of the endoscope. For example, the button may at least partially circumscribe the proximal handle section of the endoscope.

Further provided is a method of using a variable direction of view endoscope, including the steps of providing an endoscope with a variable direction of view adjustable over plurality of view angle positions relative to the endoscope, and actuating a single button to adjust the view angle from a first one of the view angle positions to a second of the view angle positions, wherein each subsequent actuation of the single button causes the view controlling device to adjust the view angle to a next one of the view angle positions.

Other objects of the invention and its particular features and advantages will become more apparent from consideration of the following drawings and accompanying detailed description.

DETAILED DESCRIPTION OF THE INVENTION

The following detailed description illustrates the invention by way of example, not by way of limitation of the principles of the invention.

Figure 1A:
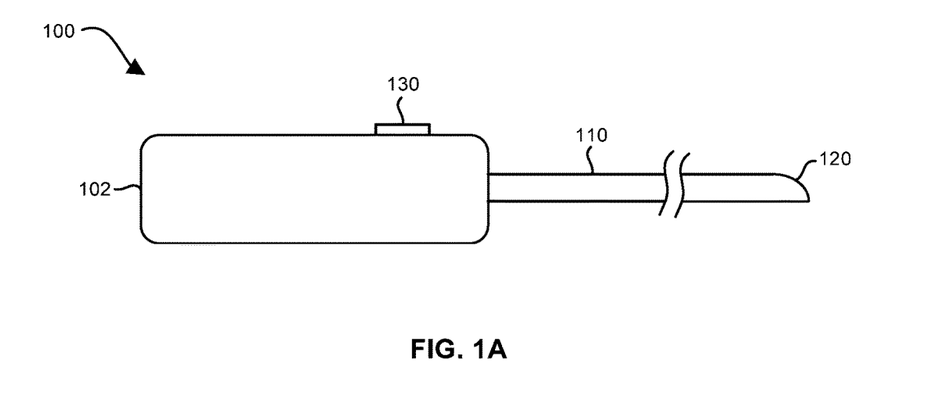
FIGS. 1A and 1B illustrate a variable view endoscope according to an exemplary embodiment of the present invention.
Figure 1B:
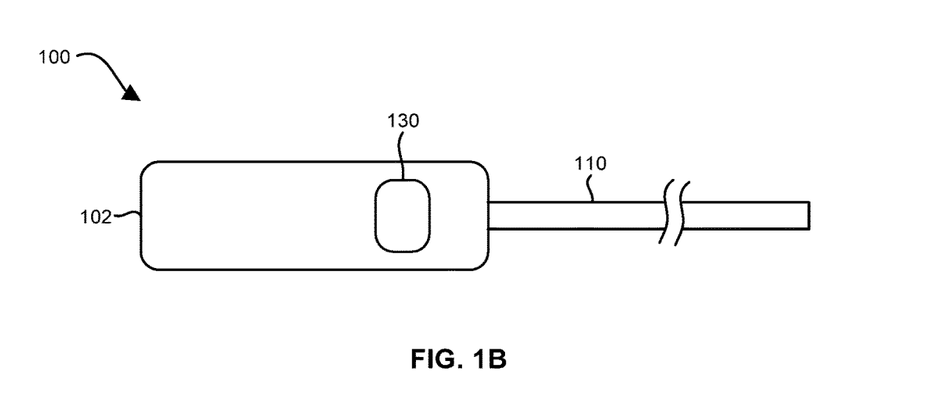

FIGS. 1A and 1B show a variable view endoscope 100 according to an exemplary embodiment of the present invention. The endoscope 100 may be one of a mechanical, electromechanical, electronic, and solid state endoscope. The endoscope 100 includes a proximal handle 102 and a shaft 110. The shaft 110 includes a distal end 120. The shaft 110 and distal end 120 may be flexible or rigid. In the exemplary embodiment, the endoscope 100 includes a single button 130 on the proximal handle 102. In other embodiments, the button 130 may be located elsewhere on the endoscope 100 or remote to the endoscope 100.

The button 130 permits users to cycle through viewing angles (or view vectors) of the endoscope 100. Unlike multiple button endoscopes, the viewing angle can be changed by pressing the same button 130 in sequence. Thus, the user can easily adjust the viewing angle without having to see the button and without risk of pressing the wrong button. The advantage of not having to be concerned about erroneous button presses greatly outweighs the disadvantage of extra button presses. There are also cost, manufacturing, and robustness advantages to having only a single button.

The viewing angles may include a fixed number of viewing angles associated with the endoscope or, in some embodiments, may be predefined or preset by the individual user and stored in a database of the endoscope system. For example, the endoscope may include fixed viewing angles of zero (0) degrees, thirty (30) degrees, forty-five (45) degrees, seventy (70) degrees, and ninety (90) degrees. Alternately, the endoscope may have a predetermined angular displacement associated with each actuation of the button 130. For example, each press of the button 130 may move change the viewing angle by ten (10) or fifteen (15) degrees. In some embodiments, the viewing angle may change continuously over a particular range (e.g., zero to ninety degrees) by holding the button 130, or by actuating a slider.

Figure 2:
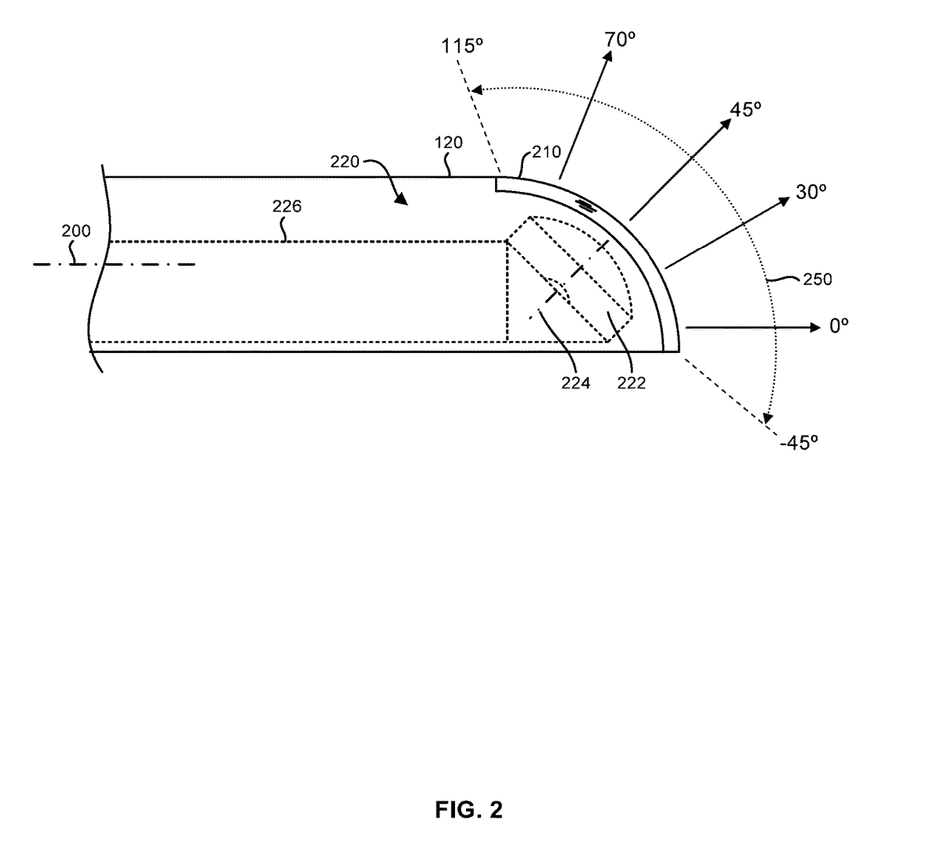
FIG. 2 illustrates a distal end of a variable view endoscope according to an exemplary embodiment of the present invention.

FIG. 2 shows the distal end 120 of the variable view endoscope 100 according to an exemplary embodiment of the present invention. The distal end 120 includes an optical system 220 having one or more optical elements 222 and a transmission system 226. In the present embodiment, the optical system 220 includes a wide-angle lens 222 as disclosed in commonly owned U.S. patent application Ser. Nos. 12/169,290 and 13/354,801, the contents of which are incorporated herein by reference. The optical center 224 of the lens 222 is angularly offset from the longitudinal axis 200 of the endoscope 100 and covers a viewing range of one-hundred and sixty degrees from negative forty-five (−45) to one-hundred and fifteen (115) degrees relative to the longitudinal axis 200. In this configuration, the wide-angle lens 222 may simultaneously gather an endoscopic image field that spans the longitudinal axis 200 and an angle greater than ninety degrees to the longitudinal axis 200. The image field gathered by wide-angle lens 222 is conveyed via the transmission system 226 to an image sensor.

The wide-angle lens 222 may capture a wide image field with discrete regions of interest over a range 250. A region of interest is an image area formed on image surface area that is a subset of the overall field of view captured by the sensor. The range 250 may include regions of interest (ROIs) at 0, 30, 45 and 70 degrees which can be selected by a user. In particular, by actuating the button 130, the user may cycle through the regions of interest or viewing angles. Each depression of the button 130 changes the region of interest to the subsequent region of interest or viewing angle. As noted above, in some embodiments, the user may also hold the button 130 to change the viewing angle (e.g., through predetermined positions or continuously through an unlimited number of viewing angles). When the last region of interest is being viewed (e.g., 70 degrees), actuating the button 130 will change the region of interest to the first region of interest (e.g., 0 degrees).

Figure 3A:
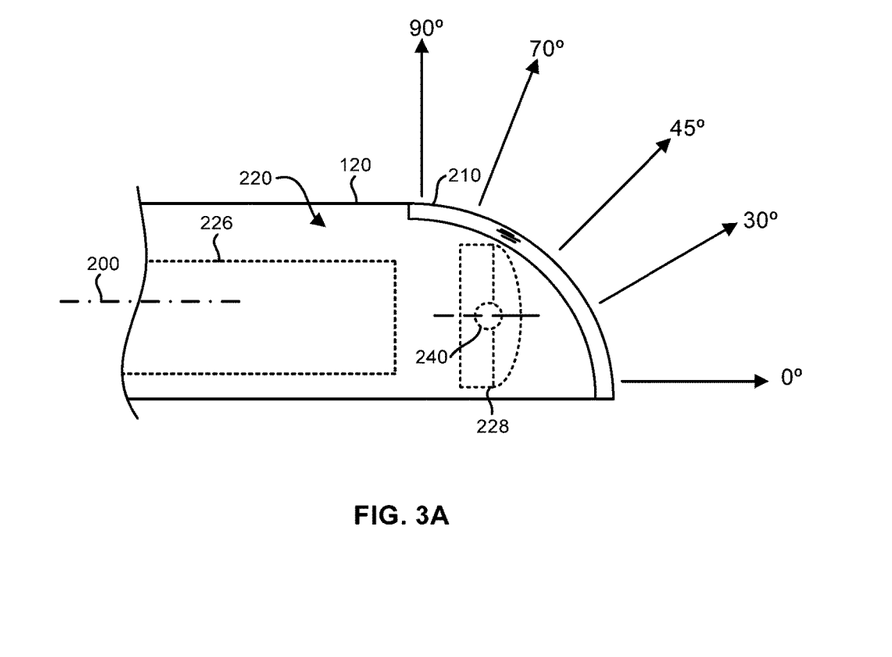
FIGS. 3A and 3B illustrate a distal end of a variable view endoscope according to an exemplary embodiment of the present invention.
Figure 3B:
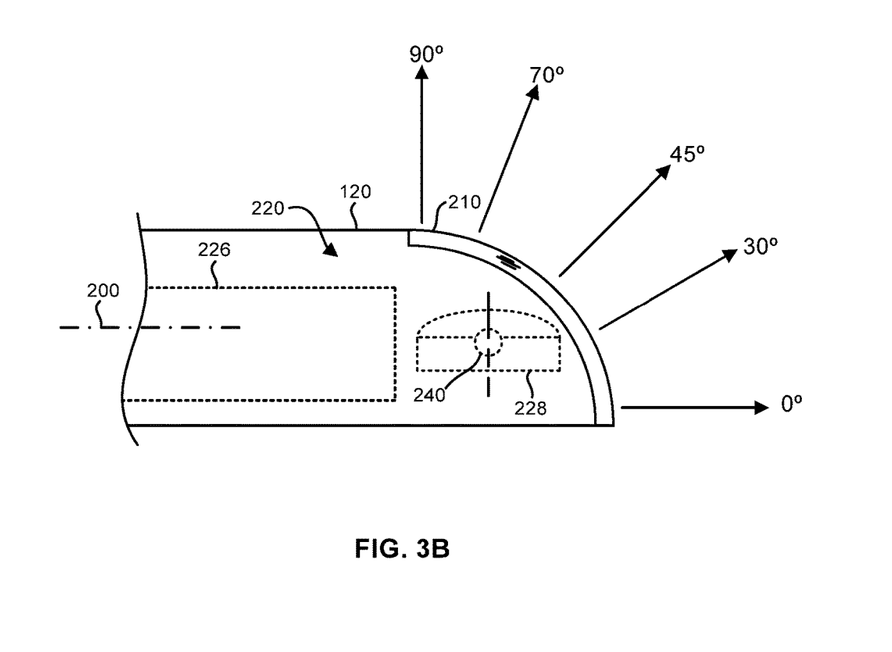

FIGS. 3A and 3B show the distal end 120 of the variable view endoscope 100 according to another exemplary embodiment of the present invention. The distal end 120 includes an optical system 220 including an image receiver 228 and a transmission system 226. The image receiver 228 may include an optical element, an image sensor, or both. The image sensor may be, but is not limited to, a CCD (charge-coupled device) or CMOS (complementary metal-oxide-semiconductor) image sensor. In the present embodiment, the receiver 228 is movable by means of a view control device or mechanism 240 to adjust the viewing angle of the endoscope 100. For example, the endoscope 100 may include any number of preset endoscope viewing angles such as 0°, 30°, 45°, 70°, and 90°. The view control device 240 may be any device or mechanism for adjusting the viewing angle and/or moving the receiver 228 known to those of skill in the art, such as a mechanical or electromechanical device controlled by the button 130.

By using the single button 130, a user can cycle through each of the available viewing angles, from a first limit (e.g., 0°) to a second limit (e.g., 90°), as the button 130 is actuated or pressed. FIG. 3A shows the image receiver 228 positioned such that the viewing angle is zero (0) degrees. FIG. 3B shows the image receiver 228 positioned such that the viewing angle is ninety (90) degrees. Adjusting the endoscope 100 from the configuration shown in FIG. 3A to the configuration shown in FIG. 3B is achieved by actuating the single button 130 four times. When the second limit is reached, the viewing angle is adjusted back to the first limit with a subsequent press of the button 130. If the desired viewing angle is zero (0) degrees but the current viewing angle is forty-five (45) degrees, the user would press the button four times (i.e., 45° to 70°, 70° to 115°, 115° to −45°, and −45° to 0°) to get back to zero (0) degrees.

In addition to changing the endoscopic line of sight or viewing angle, the single button 130 can also be used for capturing images, which is an important aspect of endoscopic surgery. For example, a short button press (e.g., less than a predetermined length of time) could advance the line of sight while a longer button press (e.g., a predetermined length of time or greater) could capture an image. In some embodiments, the image capture occurs after the button 130 has been depressed for the predetermined length of time. In other embodiments, the image capture occurs when the button 130 is released after having been held down for the predetermined length of time. These alternatives may be customized according to user preference. Pressing a button applies a force to the endoscope which may temporarily disturb the position of the endoscope 100. Such a disturbance is undesirable when taking a picture, both because it might cause a blurred image and because it could affect the present view. Therefore, if the capture happens after the button press, the surgeon will have had a chance to re-stabilize the endoscope by the time the shot is taken. Alternatively, a user may want the picture to snap upon release of the button because the user then knows and controls exactly when the capture occurs. Capturing the image upon release of the button also has the advantage that there is minimal disruption of endoscope position and stability because the only disturbance comes from the very small force of the button pushing back on the surgeon's finger as the button is released.

In some embodiments, the single button 130 is programmable to perform additional functions, such as video capture, illumination control, and/or image leveling. Each function may be assigned to a particular depression length. In some embodiments, the single button 130 is programmed for two or more of the most important and most frequent actions taken by the surgeon or surgical team, such as capturing an image, changing the viewing angle, recording video, turning insufflators on/off, changing illumination intensity, and turning illumination off. As one of skill in the art will understand, many of these functions apply to all endoscopes and thus the invention is not limited to variable view endoscopes.

Figure 4A:
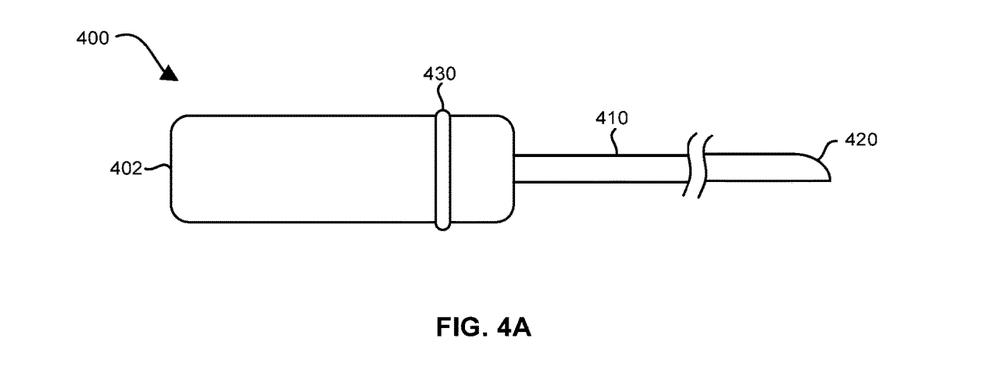
FIGS. 4A and 4B illustrate a variable view endoscope according to an exemplary embodiment of the present invention.
Figure 4B:
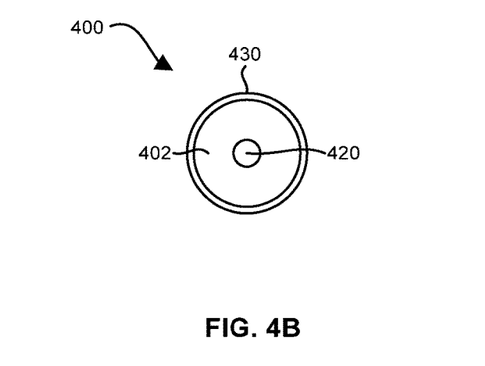

FIGS. 4A and 4B show another endoscope 400 according to an exemplary embodiment of the present invention. The endoscope 400 may be one of a mechanical, electromechanical, electronic, and solid state endoscope. The endoscope 400 includes a proximal handle 402 and a shaft 410. The shaft 410 includes a distal end 420. The shaft 410 and distal end 420 may be flexible or rigid.

In the exemplary embodiment, the endoscope 400 includes a single button 430 that circumscribes the proximal handle 402. The button 430 may partially or completely circumscribe the handle 402 such that the button is readily accessible in any configuration. Thus, in this embodiment, the button 430 is always in the same generally location regardless of whether the handle 402 has been rotated.

Figure 5:
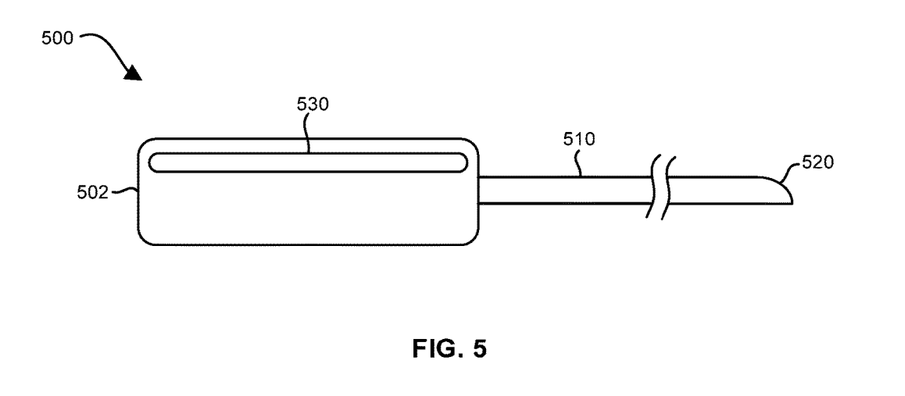
FIG. 5 illustrates a variable view endoscope according to an exemplary embodiment of the present invention.
Figure 6:
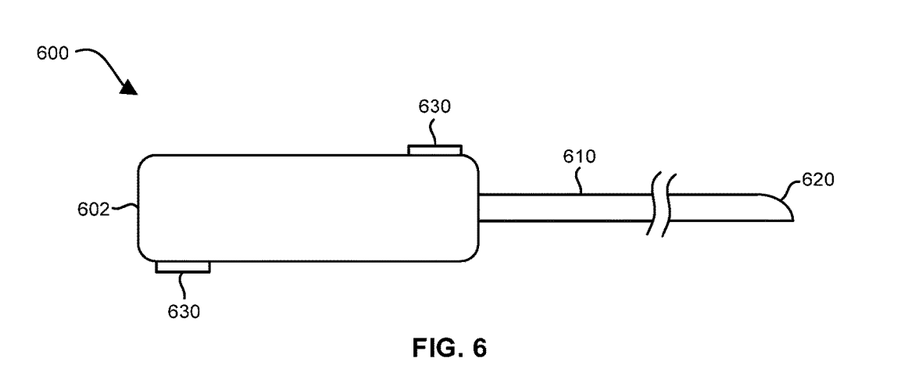
FIG. 6 illustrates a variable view endoscope according to an exemplary embodiment of the present invention.

Other button locations and configurations may be employed according to user preferences and/or to accommodate different handle geometries and different surgical procedures. For example, the button may be an elongated button 530 extending lengthwise along the handle 502 as shown in FIG. 5. In some embodiments, the element 530 functions as a slider to allow the user to continuously change the viewing angle over a particular range (e.g., with predetermined viewing angles, angular steps, or a continuous range). In another embodiment shown in FIG. 6, an endoscope 600 includes two or more buttons distributed about different locations on a handle 602 (e.g., top and bottom and/or proximal end and distal end), each having the same functionality. Thus, the advantages of using a single button for cycling through all of a plurality of viewing angles may be achieved irrespective of where the user grips the handle 602.

Although the invention has been described with reference to a particular arrangement of parts, features and the like, these are not intended to exhaust all possible arrangements or features, and indeed many modifications and variations will be ascertainable to those of skill in the art.

What is claimed is:

1. A variable direction of view endoscope system, comprising:
   an endoscope having an image receiver with a variable direction of view adjustable over a viewing range bound by a first limit and a second limit, said variable direction of view being adjustable in only one direction over the viewing range with a wrap-around from the second limit directly back to the first limit;
   the endoscope having only one control interface, said one control interface is configured to adjust the variable direction of view of the image receiver and to capture images via said endoscope, wherein actuating said one control interface issues a command to a view control device to advance the variable direction of view sequentially through the viewing range from a first one of a plurality of view angle positions to a second one of the plurality of view angle positions, wherein when the image receiver is at the second limit of the viewing range, one same actuation of said one control interface issues the command and adjusts the image receiver back to the first limit of the viewing range;
   wherein said one control interface is a button.

2. The endoscope system according to claim 1, wherein the viewing range is zero degrees to ninety degrees.

3. The endoscope system according to claim 1, wherein the image receiver includes one of a CCD image sensor and a CMOS image sensor.

4. The endoscope system according to claim 1, wherein a short button press, pressed for less than a predetermined amount of time, adjusts the view angle, while a long button press, pressed for at least the predetermined amount of time, captures an image.

5. The endoscope system according to claim 1, wherein said one button is on a proximal handle section of said endoscope.

6. The endoscope system according to claim 5, wherein said button at least partially circumscribes the proximal handle section of said endoscope.

7. The endoscope system according to claim 1, wherein said one button is programmed such that actuation of said one button by pressing and releasing said one button advances the variable direction of view to a next one of a plurality of positions in the viewing range.

8. The endoscope system according to claim 7, wherein actuation of said one button by pressing and holding said one button cycles the variable direction of view through each of the plurality of positions in the viewing range.

9. A variable direction of view endoscope system, comprising:
an endoscope having an image receiver with a variable direction of view adjustable over a viewing range bound by a first limit and a second limit, said variable direction of view being adjustable in a single direction over the viewing range with a wrap-around from the second limit directly back to the first limit;
only one mechanism disposed on the endoscope for receiving user input to adjust the variable direction of view of the image receiver and to capture images via said endoscope, said mechanism consisting of only one button, actuation of the one button issuing a command to a view control device to advance the variable direction of view sequentially in a direction towards the second limit from a first one of a plurality of view angle positions to a second one of the plurality of view angle positions and, once the second limit is reached, back to the first limit with one same actuation of the one button.

10. The endoscope system according to claim 9, wherein a short button press, pressed for less than a predetermined amount of time, adjusts the view angle, while a long button press, pressed for at least the predetermined amount of time, captures an image.

11. The endoscope system according to claim 9, wherein an image is captured once the one button is released after having been held down for a predetermined amount of time.

12. The endoscope system according to claim 9, wherein the endoscope is one of a mechanical, electromechanical, electronic, and solid state endoscope.

13. The endoscope system according to claim 9, wherein the viewing range is zero degrees to ninety degrees.

14. The endoscope system according to claim 9, wherein said one button is on a proximal handle section of said endoscope.

15. The endoscope system according to claim 9, wherein actuation of the one button by pressing and releasing the one button advances the variable direction of view to a next one of a plurality of positions in the viewing range, and actuation of the one button by pressing and holding the one button cycles the variable direction of view through each of the plurality of positions in the viewing range.

16. A variable direction of view endoscope system, comprising:
an endoscope having an image receiver with a variable direction of view adjustable over a viewing range bound by a first limit and a second limit;
the endoscope having only one button, said one button for adjusting the variable direction of view of the image receiver, wherein actuating said one button issues a command to advance the variable direction of view sequentially through the viewing range, wherein said one button provides only one direction traverse of the viewing range with a wrap-around to the first limit once the second limit has been reached; and
a view control device, wherein said one button issues the command to the view control device to adjust the variable direction of view of the image receiver.

* * * * *